US00PP31687P3

(12) United States Plant Patent
Maillard et al.

(10) Patent No.: US PP31,687 P3
(45) Date of Patent: Apr. 21, 2020

(54) NECTARINE TREE NAMED 'CAKERUMBA'

(50) Latin Name: ***Prunus persica* var *nucipersica***
Varietal Denomination: CAKERUMBA

(71) Applicant: AGRO SELECTIONS FRUITS, Elne (FR)

(72) Inventors: Arsène Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 16/350,463

(22) Filed: Nov. 20, 2018

(65) Prior Publication Data

US 2019/0159389 P1 May 23, 2019

(30) Foreign Application Priority Data

Nov. 23, 2017 (QZ) ..... PBR 2017/3053

(51) Int. Cl.
*A01H 5/08* (2018.01)
*A01H 6/74* (2018.01)

(52) U.S. Cl.
USPC ..... Plt./188
CPC ..... *A01H 6/7454* (2018.05)

(58) Field of Classification Search
USPC ..... Plt./188
CPC ..... A01H 5/08; A01H 5/0856; A01H 5/00; A01H 6/74; A01H 6/7481; A01H 6/7454
See application file for complete search history.

(56) References Cited

U.S. PATENT DOCUMENTS

PP23,357 P3 * 1/2013 Maillard ..... A01H 6/7454 Plt./188

* cited by examiner

*Primary Examiner* — June Hwu
(74) *Attorney, Agent, or Firm* — Birch, Stewart, Kolasch & Birch, LLP

(57) ABSTRACT

A new and distinct variety of white flat nectarine tree denominated 'CAKERUMBA' has fruits with high eating quality and very long shelf life without alteration before and after harvesting, with a semi-sweet white flesh, with a slightly red pigmentation around the stone cavity, a completely closed pistil cavity and an attractive luminous skin with a high percentage of purple red blush on skin surface, on a red background.

3 Drawing Sheets

Botanical classification: *Prunus persica* var *nucipersica*.
Variety denomination: 'CAKERUMBA'.

This application claims priority of Community plant variety right No. 2017/3053 filed on Nov. 23, 2017 which is hereby incorporated by reference in its entirety.

The new variety named 'CAKERUMBA' is also known as 26.18.109.15 NBPL ASF 15215. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and finally the year of selection. Then before being named 'CAKERUMBA', the provisional reference of this white flat nectarine tree variety was 26.18.109.15 NBPL, corresponding to the tree 109 located in line 18 of the parcel 26 and selected during the year 2015. The letters "NBPL" are related to the first letters of the type of tree in French (NBPL for "Nectarine Blanche PLate", that means "white flat nectarine"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'CAKERUMBA', the clone reference was 'ASF15215'.

BACKGROUND OF THE NEW VARIETY

The present invention relates to a new and distinct variety of white flat nectarine tree, *Prunus persica* (L.) Batsch, which has been given the variety denomination 'CAKERUMBA'.

This new tree produces fruits with a long shelf life without alteration both on the tree after growth completion and after harvesting, very good eating quality, semi-clingstone white flesh fruits, generally with a very slightly red pigmentation around the stone cavity, in a star shape, for fresh market in August in the Pyrénées-Orientales department, France.

ORIGIN OF THE VARIETY

The 'CAKERUMBA' white flat nectarine tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen. Summer is dry with a few thunderstorms.

The 'CAKERUMBA' variety results from a pollinated and controlled cross between a white nectarine tree named 'NECTARPERF' (U.S. Plant Pat. No. 23,357) which was used as a seed parent (or female parent) and the 'CAKEDELICE' (U.S. Plant Pat. No. 25,632) white flat nectarine tree which was used as the pollen parent (male parent).

The 'CAKERUMBA' variety was obtained by hybridizing and propagated by grafting on a 'INRA GF677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

Every known type of grafting adapted to the nectarine tree may be performed on the new tree. Especially, the type of grafting will depend on the grafting period and the propagation mode which is used by the nursery owner. Thus, the grafting period may be micrografting at any moment of the year if the grafting is performed in greenhouse, dormant eye shield budding in August or September, growing eye shield budding in June or July.

SUMMARY OF THE VARIETY

The new and distinct variety 'CAKERUMBA' white flat nectarine tree blooms early in March near Elne in the Pyrénées-Orientales department, France. The blooming period is considered medium. However, it was observed that its late date of blooming seems to be highly dependant on climatic conditions.

The first fruit of 'CAKERUMBA' ripens generally medium to late during the season, generally at the end of August, but sometimes earlier. More particularly, it usually ripens between August $4^{th}$ and August $30^{th}$. However, it was observed that its date of maturity seems to be highly dependant on climatic conditions.

DESCRIPTION OF THE DRAWINGS

In the accompanying drawing, which are as nearly true as it is reasonably possible to make in a color illustration of this type.

Figure 1:
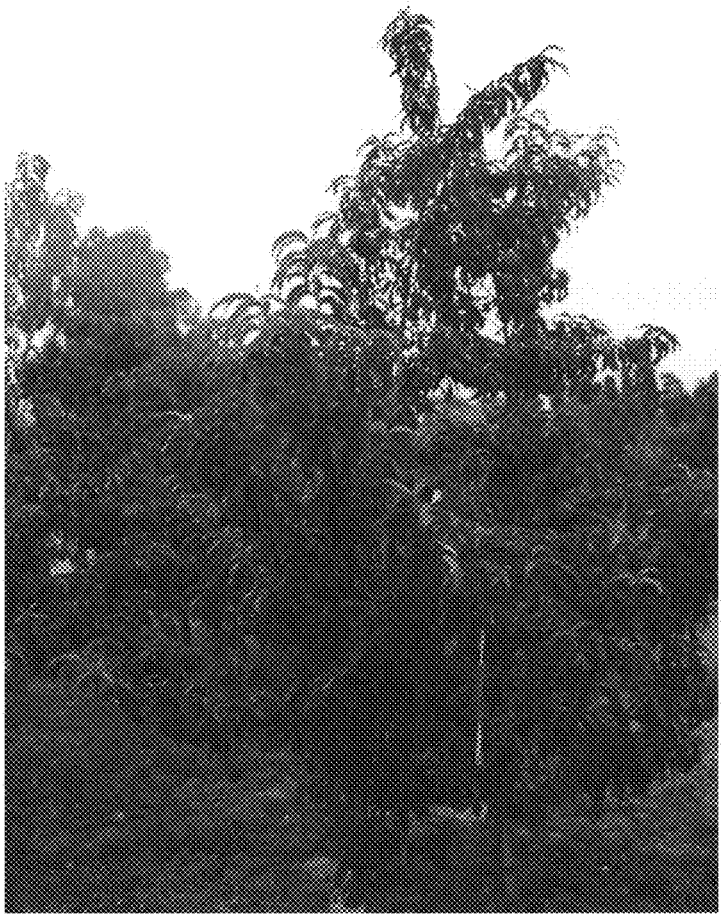
FIG. 1 is a color photograph that shows a typical specimen of a tree of the new variety 'CAKERUMBA' in orchards, with branches bearing fruits.
Figure 2:
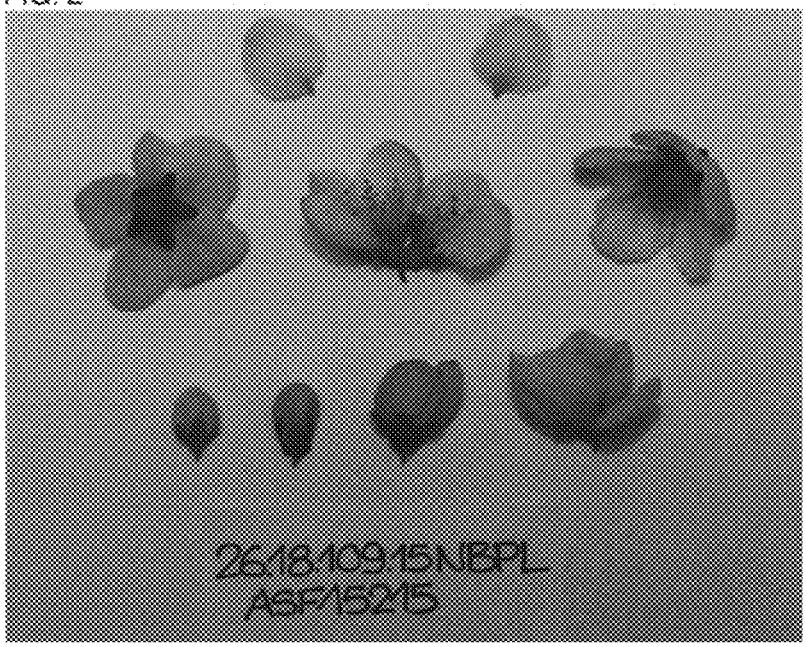
FIG. 2 is a color photograph which depicts the flower buds at different development stages, and the reverse and side view of the flower and the reproductive organs with petals removed, of the new variety also referenced as "26.18.109.15 NBPL ASF 15215".
Figure 3:
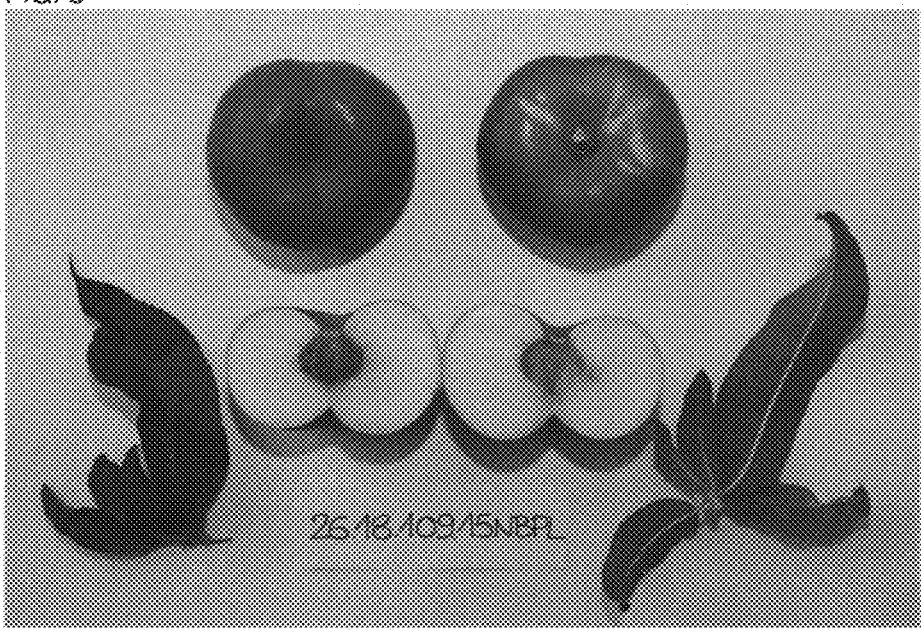
FIG. 3 is a color photograph which shows the upper and lower sides of leaves and three typical specimens of the fruit, one having been cut in halves with the stone being left in one of the halves for depicting leaves, fruit flesh, the stone and the stone cavity of the new variety also referenced as "26.18.109.15 NBPL".
Figure 4:
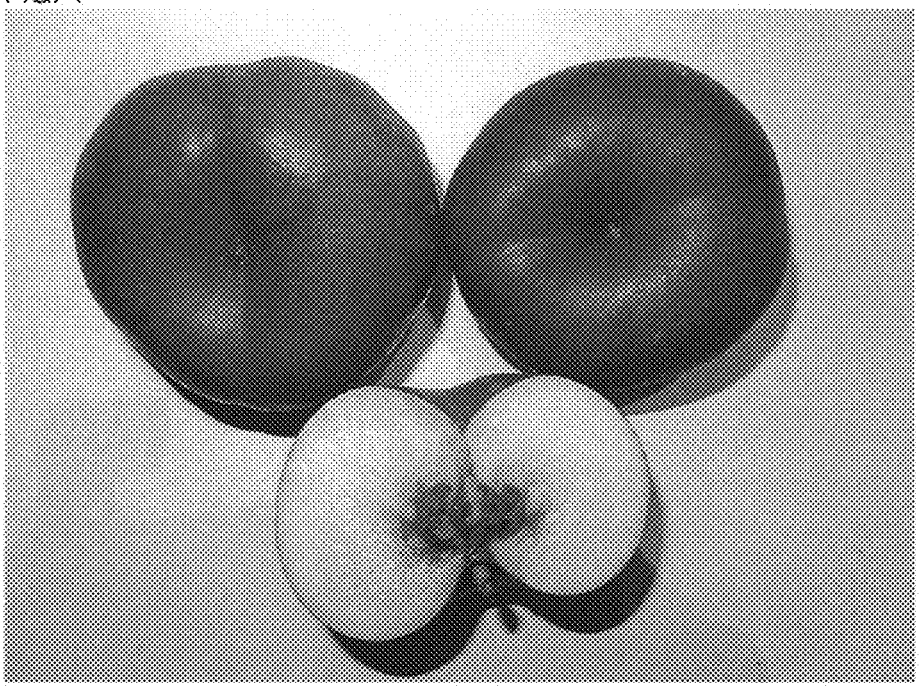
FIG. 4 is a color photograph that shows a close view of typical specimens of the fruit of the new variety 'CAKERUMBA' at ripening time, one having been cut in a half with the stone left in its cavity.
Figure 5:
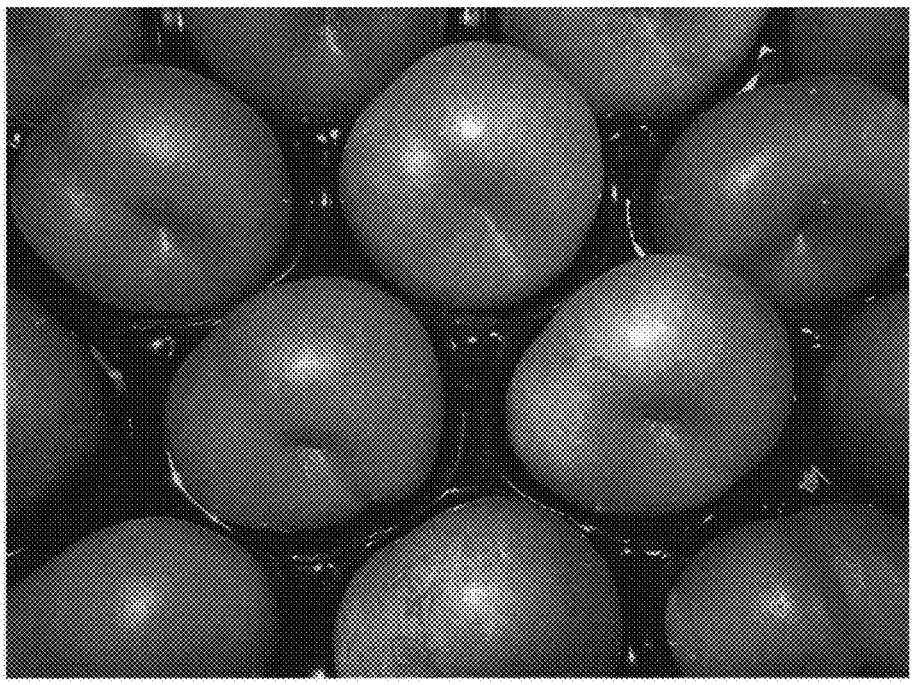
FIG. 5 is a color photograph that shows a close view of typical specimens of the fruit of the new variety 'CAKERUMBA' at ripening time
Figure 6:
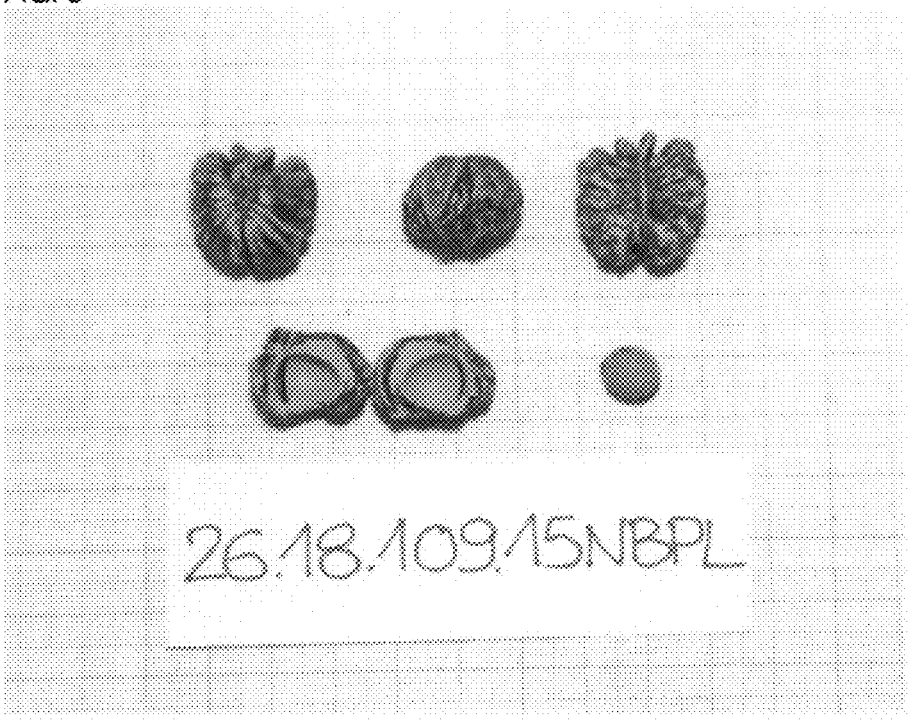
FIG. 6 is a color photograph showing different views of the stone of the new variety, also referenced as "26.18.109.15 NBPL", one having been cut in halves with the kernel removed.

The enclosed photographs show plants in their third growing season for trees, trunk, leaves, fruits and stone and plants in their fourth growing season for flowers.

Due to chemical development, processing and printing, the flowers, stones and fruits depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'CAKERUMBA' is high, due to fruit very long shelf life without alteration after harvesting.

Trees are medium vigorous and large stature half-standing in a semi-flared aspect.

The anthocyanic coloration of flowering shoot is present excluding brushwood side away from sun. The time of beginning of flowering is considered medium; flowering begins early in March. The type of flower is showy (rosette) with medium to large petal size. Petals are pink. Leaf glands are present and reniform. The fruit flesh is white and generally with a very slightly red pigmentation around the stone cavity in a star-shape. The fruit skin is thick, with a luminous purple red blush on a red background. The stone is semi-clingstone and his size is small. Fruit taste is semi-sweet, very aromatic and with a high level of sugars.

Compared to its female parent 'NECTARPERF' variety (U.S. Plant Pat. No. 23,357), which produces round fruits, the fruits of the new variety 'CAKERUMBA' are flat. The fruits of the new variety 'CAKERUMBA' ripen 10 days earlier than the fruits produced by 'NECTARPERF'.

Compared to 'CAKEDELICE' (U.S. Plant Pat. No. 25,632) variety, which is the male parent, the fruits of 'CAKERUMBA' variety ripen two weeks later. The trees of the new variety 'CAKERUMBA' produces 50 to 55 flowers per linear meter at blossoming, whereas the trees of 'CAKEDELICE' variety produces approximately 40 to 45 flowers per linear meter. The fruits of the new variety 'CAKERUMBA' have a more attractive appearance, their shape being rounder and more regular than the fruits of 'CAKEDELICE'.

DETAILED DESCRIPTION

Referring more specifically to the pomological details of this new and distinct variety of white flat nectarine tree, the following was observed on trees in their third growing season (second year of production) for trees, trunk, leaves, fruits, stone and on trees in their fourth growing season (third year of production) for flowers, under the ecological conditions prevailing at the orchards located near the town of Elne, Pyrénées-Orientales departement, France. All observations have been done on rootstock cultivars. Used rootstocks were 'INRA GF677' (non-patented) trees. All major color code designations are by reference to The R.H.S. Colour Chart (Fourth Edition) provided by The Royal Horticultural Society of Great Britain.

Tree:

*Size.*—

*Generally.*—Considered large. The tree size the first year was approximately 200 to 280 cm. The tree was pruned during each following dormant season to a height of approximately 250 cm. Current season shoots growth could reach 80 cm. The tree size from the second year (second and next years) reached a final height of 330 cm including current season shoots length. The tree size is consistently reduces to 250 cm the next years.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor.*—Considered medium.

*Productivity.*—Very Productive. Fruit set is spaced by thinning to develop the remaining fruit into the desired market sized fruit. The number of the fruit set varies with the prevailing climatic conditions and cultural practices employed during the bloom period, and is therefore not distinctive of the present variety. A reduce vegetation, obtained with pruning or green pruning, approximately 1 month or 1 month ½ before harvesting flat fruits, significantly promotes fruit qualities, especially growth, color and firmness. Moreover, contamination risks due to *Monilia* or rot are significantly reduced. 'CAKERUMBA' variety is not much sensitive to cracking of pistil cavity, to cork formation into peduncle cavity or to *Monilia.*

*Bearer.*—Very regular. The fruit distribution is considered homogenous on mixed branches and spurs having more than 1 year. Thinning of 2 fruits out of 3 was necessary for the tree valorisation. Thinning was necessary every year during the years of observation.

*Form.*—The 'CAKERUMBA' variety has naturally a semi-flared shape.

*Density.*—Considered dense.

*Hardiness.*—The present tree was grown and evaluated in France. The variety appears to be hardy under the central Pyrénées-Orientales departement typical climatic conditions. Experimentations on the same orchard in Elne, Pyrénées-Orientales department, with winter chilling requirement below 7.2° C. comprised between 700 hours and 1200 hours according to the specificities of the year, namely 1076 hours in 2012-2013, 767 hours in 2013-2014, 552 hours in 2014-2015, 721 hours in 2015-2016, and 784 hours in 2016-2017 showed a good behaviour of the tree in all cases. No damages were caused by ascertained temperatures as low as −12 degrees Celsius in winter. The tree was also very resistant to frosty springtime weather. Traditionally, flat fruits are more sensitive to critical low temperatures and to climatic variations, because of the flower morphology in which the ovule is less protected than in the classical round fruits. Thus, areas not much exposed to frost are recommended for trees growth. However, 'CAKERUMBA' trees seem to be very resistant to critical frosty weather.

Trunk:

*Diameter.*—Approximately 48.0 to 54.0 millimeters in diameter when measured at a distance of approximately 20 centimeters above the soil level on 3$^{rd}$ growing season.

*Bark texture.*—Considered slightly rough, with lenticels.

*Lenticels.*—Numerous lenticels are present. The number of lenticels reaches 2 lenticels per cm$^2$. The lenticels range in size from approximately 4.0 to 6.0 millimeters in width, and about 2.0 to 3.0 millimeters in height.

*Lenticel color.*—The lenticels have a light orange color (RHS Greyed Orange 165 B).

*Bark coloration.*—The bark has a light brown color (RHS Greyed Orange 165 A) slightly darker than the lenticel color.

Branches:

*Size.*—Mature branches and current season shoots are considered medium for the variety.

*Diameter.*—Average as compared to other nectarine varieties. The current season shoots have a diameter from 4.0 to 6.0 millimeters, and mature branches have a diameter from 8.0 to 10.0 millimeters.

*Surface texture.*—Average, wood which is several years old has no furrowed appearance.

*Crotch angles.*—Primary branches are considered variable, but the crotch angles are generally about 45 degrees from the horizontal axis, for both current season shoots and mature branches. This particular characteristic is not considered distinctive of the variety, however.

*Current season shoots.*—

*Internode length.*—Generally between 15.0 and 20.0 millimeters.

*Color.*—The color of new shoot tips is considered light green (RHS Yellow Green 145 A) on lower part of new shoot tips, whereas the upper part is darker and colored in brown-purple more or less deep (RHS Greyed Orange 176 A), depending on the level on the tip and the sunlight exposure.

*Texture.*—Smooth, without lenticels.

*Mature branches.*—

*Internode length.*—Generally between 21.0 and 24.0 millimeters.

*Color of mature branches.*—Brown (RHS Grey Brown N 199 B).

*Texture.*—Smooth to rough, with small lenticels.

*Lenticels.*—The number of lenticels on mature branches reaches 2 lenticels per cm$^2$. The lenticels range in size from approximately 2.0 to 2.5 millimeters in width, and about 1.0 to 1.5 millimeters in height.

*Lenticel color.*—The lenticels on mature branches have a beige color (RHS Greyed Orange 164 B to RHS Greyed Orange 164 C).

*Lenticel shape.*—Lenticels on mature branches are round-stretched in shape.

Leaves:

*Size.*—Considered medium for the species. The ratio leaf length/leaf width is 3.61. This ratio is calculated with the medium length of five measures taken on five different leaves (129.8 millimeters), divided by the medium width of also five measures (36.0 millimeters).

*Leaf length*.—Approximately 120.0 to 139.0 millimeters with leaf petiole. The medium length is about 129.8 millimeters.

*Leaf width*.—Approximately 33.0 to 40.0 millimeters. The medium width is 36.0 millimeters.

*Leaf form in sectional view*.—Concave.

*Leaf form*.—Lanceolate.

*Leaf tip form*.—Short, pointed and acuminate.

*Leaf color*.—

*Upper leaf surface*.—Yellow green (RHS Yellow Green 147 A).

*Lower surface*.—A lighter green (RHS Yellow Green 147 B) than the upper leaf surface color.

*Leaf texture*.—Both upper and lower leaf surfaces are considered smooth and glabrous.

*Leaf venation*.—Pinnately veined.

*Mid-vein*.—

*Color*.—Light green, almost cream white (RHS Yellow Green 145A). The color may evolve with maturity.

*Leaf margins*.—Slightly undulating.

*Form*.—Leaf margins are considered slightly dentate.

*Uniformity*.—Leaves are isolated or grouped by 2 or 3. In this last case, one leaf of normal size is found with one or two smaller leaves (at least 50% smaller).

*Leaf petioles*.—

*Size*.—Considered medium.

*Length*.—About 9.0 to about 10.0 millimeters.

*Diameter*.—About 2.0 millimeters.

*Petioles color*.—

*Upper petiole surface*.—Light green (RHS Yellow Green 144 B).

*Lower surface*.—Light green (RHS Yellow Green 145 B).

*Leaf glands*.—

*Size*.—Considered medium. Their length is about 1.0 to 1.5 millimeters and their width is about 1.0 millimeter.

*Number*.—Generally 2 glands per leaf.

*Type*.—Reniform.

*Margins*.—Smooth and regular.

*Color*.—On young leaves, leaf glands color is considered a light green (RHS Green 145 B). On older leaves, leaf glands color turns to a dark brown (RHS Grey Brown 199 A to RHS Grey Brown 199 B).

*Margins*.—Smooth and regular.

*Leaf stipules*.—

*Generally*.—No leaf stipules were observed. But as seen in the characteristic relative to the leaves uniformity, it is possible to find leaves by groups of 2 or 3, with a normal-size leaf and smaller ones.

*Time of beginning of leaf bud burst*.—Generally considered medium.

Flowers:

*Flower buds*.—

*Generally*.—At pre-floral stage of development, the floral buds are round in form with a round tip. Their form is evolving until blooming, with variables dimensions. Just before blooming, floral buds are approximately 10.0 to 11.0 millimeters wide and approximately 16.0 to 18.0 millimeters long. The distribution of the flower buds is considered homogenous on the trees.

*Color*.—This characteristic is dependent upon the proximity to bloom. At pre-floral stage of development, the bottom of the flowers buds, the calyx or flower receptacle, is of purple-brown color (RHS Greyed Purple 187) on its outer face. The inner surface of the calyx is considered orange yellow (RHS Yellow Orange 22 A). The corolla, formed by the petals, is generally of pink color (RHS Red Purple 65 A to RHS Red Purple 65 B). Petals color shows an evolution until the end of flowering.

*Hardiness*.—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom*.—The blooming time generally begins early in March. The first bloom was observed on Mar. 5, 2016.

*Blooming time*.—Considered medium in relative comparison to other commercial nectarine cultivars grown in the Pyrénées-Orientales departement, France. The date of full bloom is observed generally at the middle of the blooming period. The date of bloom varies slightly with climatic conditions and cultural practices. Thus the full bloom was observed in 2016, from March $5^{th}$ until March $12^{th}$, then from March $4^{th}$ until March $11^{th}$ in 2017.

*Duration of bloom*.—Approximately 8 days. This characteristic varies slightly with the prevailing climatic conditions.

*Flower type*.—The variety is considered to have a showy type flower (rosette).

*Flower size*.—Considered medium to large. Flower diameter at full bloom is approximately 38.0 to 42.0 millimeters.

*Bloom quantity*.—Considered very abundant, approximately between 50 and 55 flowers per meter, with a high rate of fruit set. The bloom is heterogeneous, and the bloom quantity is more important on the top of the tree.

*Flower bud frequency*.—Generally 2 flower buds appear per node, occasionally 1.

*Petal size*.—

*Generally*.—Considered medium to large.

*Length*.—Generally between 22.0 and 23.0 millimeters.

*Width*.—Generally between 19.0 and 20.0 millimeters.

*Petal form*.—Round-shaped.

*Petal count*.—Generally 5.

*Petal arrangement*.—Overlapping.

*Petal texture*.—Smooth.

*Petal color*.—Both surfaces of the petal are colored with a pink (RHS Red Purple 65 A to RHS Red Purple 65 B) color.

*Fragrance*.—Sweet.

*Petal claw*.—

*Form*.—The claw is considered to have a narrow form.

*Length*.—About 1.5 to 2.5 millimeters.

*Width*.—About 1.5 millimeter at the base.

*Color*.—Considered dark pink (RHS Red Purple 60 B to RHS Red Purple 60 C), darker than the petal color.

*Petal margins*.—Generally considered moderately undulate.

*Petal apex*.—

*Generally*.—The petal apices are generally wide dome-shaped.

*Flower pedicel*.—

*Length*.—Considered medium to large and having an average length of approximately 3.0 to 4.0 millimeters.

*Diameter*.—Considered average, approximately 1.0 to 1.5 millimeters.

*Color*.—Light green (RHS Yellow Green 144 B to RHS Yellow Green 144 C).

*Calyx*.—

*Internal surface texture*.—Smooth and glabrous.

*Color*.—At the stage F of blooming, when the flower is open, the inner surface of the calyx, or flower receptacle, is yellow green (RHS Yellow Green 153 C) to yellow orange (RHS Yellow Orange 22A). The outer surface of the calyx is considered of purple-brown (RHS Greyed Purple 187 A) color.

*Sepals*.—

*Sepal count*.—Usually five.

*Surface texture*.—The outer surface has a short, fine pubescent texture.

*Size*.—Medium to large.

*Length*.—Approximately 5.0 to 7.0 millimeters.

*Width*.—Approximately 4.0 to 5.0 millimeters.

*Form*.—Conic, with a round tip.

*Margins*.—Smooth.

*Color*.—At the stage F of blooming, the lower surface of the sepals is considered of purple-brown color (RHS Greyed Purple 187 A). The upper surface of the sepals is considered greenish (RHS Yellow Green 146 A).

*Average number of stamens per flower*.—Approximately 34 to 40 stamens per flower. The stamens are shorter than petals, so the position of the stamens when compared to petals is below.

*Anthers*.—

*Generally*.—Small in length.

*Shape*.—Reniform.

*Color*.—Anthers are colored with a red (RHS Orange Red N34 A) color. The color may evolve with maturity to turn in a yellow color.

*Pollen production*.—Pollen is abundant, and has a yellow color (RHS Yellow 12 A) which may evolve with maturity. The present variety is considered auto-fertile (self-pollinating).

*Pollination*.—Pollen is abundant and autofertile, good compatibility in controlled hybridization.

*Filaments*.—

*Size*.—Medium length, between 14.0 and 18.0 millimeters in length. Filaments length is generally the same or slightly higher than the pistil's length (considered without the ovary).

*Color*.—Considered white (RHS White 155 D) to pink (RHS Red Purple 59 D). The color becomes darker during the blooming.

*Pistil*.—

*Number*.—Usually 1.

*Generally*.—Average in size.

*Length*.—Approximately 16.0 to 17.0 millimeters including the ovary. The pistil's length is generally the same or smaller than the filaments length, the pistil's length being considered without the ovary.

*Color*.—Considered a very pale green to almost yellow (RHS Yellow Green 150 B).

*Stigma*.—Approximately 1.5 millimeters in diameter, with a greenish yellow color (RHS Yellow Green 151 C to RHS Yellow Green 151 D).

*Ovary*.—Approximately 1.5 to 2.0 millimeters in height. The diameter of the ovary is about 1.5 to 2.0 millimeters. The color is considered green (RHS Yellow Green 144 C).

*Pubescence*.—No pubescence.

Fruit:

*Maturity when described*.—Very firm in ripe conditions (shipping ripe).

*Date of first picking*.—Aug. 22, 2015.

*Date of last picking*.—The date of harvest varies slightly with the prevailing climatic conditions. The 'CAKERUMBA' variety has a medium to late date of picking, and a grouped maturity. The maturity is grouped within 7 to 9 days and the harvest is generally performed in two runs. Last known picking times carry on from August $22^{nd}$ to Aug. 30, 2015, then from August $22^{nd}$ to Aug. 30, 2016 and then from August $4^{th}$ to Aug. 15, 2017.

*Size*.—

*Generally*.—Homogeneous in size, A (with a diameter between 67.0 and 73.0 millimeters) or 2A (with a diameter between 73.0 and 80.0 millimeters). Considered medium to large.

*Average cheek diameter*.—Approximately 65.0 to 80.0 millimeters.

*Average axial diameter*.—Approximately 42.0 to 44.0 millimeters.

*Typical weight*.—Generally about 120.0 to 130.0 grams. This characteristic is high dependent upon the prevailing cultural practices, and therefore is not particularly distinctive of the variety.

*Fruit form*.—

*Generally*.—Round and flattened, generally with few bump. The fruit is generally uniform in symmetry, viewed from the suture's plane.

*Suture*.—

*Fruit suture*.—Wide-mouthed and slightly marked, extending from the base to the apex. No apparent callousing or stitching exists along the suture line. Not pointed.

*Color*.—The suture has generally a similar color to the whole fruit color, a luminous purple red (RHS Greyed Purple 185 A or RHS Greyed Purple 187 B).

*Ventral surface*.—

*Form*.—Smooth.

*Apex*.—Slightly depressed.

*Base*.—Semi-flared, shallow.

*Stem cavity*.—Average depth of the stem cavity is about 8.0 to 12.0 millimeters. Average width is about 15.0 to 17.0 millimeters.

*Fruit skin*.—

*Thickness*.—Considered thick and strong, and the adherence of skin to flesh is strong to medium, depending on the fruit maturity.

*Texture*.—Smooth.
*Taste*.—Semi-sweet, sugary.
*Tendency to crack*.—None observed.
*Color*.—
*Blush color*.—This blush color is a luminous purple red (RHS Greyed Purple 185 A or RHS Greyed Purple 187 B). The purple red blush covers 75 to 85% of the fruit skin surface on a red background (RHS Greyed Red 179 A) on approximately 15% to 25% of the fruit skin surface. The percentage of the blush on the fruit skin surface can vary and is generally dependent upon the prevailing conditions under which the fruit was grown.
*Ground color*.—The ground color covers approximately 15% to 25% of the fruit skin surface, and is considered red (RHS Greyed Red 179 A).
*Pattern of the fruit skin over color*.—Solid flush on 75 to 85% of the fruit skin surface.
*Fruit stem*.—Medium in length, approximately 8.0 to 9.0 millimeters.
*Diameter*.—Approximately 4.0 millimeters.
*Color*.—Pale green (RHS Yellow Green 145 A).
*Flesh*.—
*Ripens*.—Very homogenously, slowly. The flesh has a long shelf life.
*Texture*.—Very firm, very dense, crunchy, melting, juicy at harvest maturity stage.
*Fibers*.—Not fibrous.
*Aroma*.—Very pronounced.
*Eating quality*.—Considered very good, aromatic.
*Flavor*.—Considered semi-sweet. The Brix is generally superior to 12 and acidity comprised between 6 and 9 meq/100 ml.
*Juice*.—Juicy to Very juicy at complete maturity.
*Brix*.—Generally 15.0 to 16.0 degrees. This characteristic varies slightly with the number of fruit per tree; prevailing cultural practices; and the surrounding climatic conditions.
*Flesh color*.—White flesh (RHS White 155 A) usually with a slightly red pigmentation (RHS Red 47 A to RHS Red 47 B) in a star shape, around the stone cavity, on approximately 5.0 millimeters.

Stone:
*Type*.—Semi-Clingstone, more or less semi-adherent depending on the fruit maturity.
*Size*.—Considered small for the variety. The stone size varies significantly depending upon the tree vigor, crop load and prevailing growing conditions.
*Length*.—Approximately 14.0 to 15.0 millimeters.
*Width*.—Approximately 20.0 to 22.0 millimeters.
*Diameter*.—Approximately 21.0 to 22.0 millimeters.
*Form*.—Flattened.
*Base*.—Straight.
*Apex*.—
*Shape*.—The stone apex is flattened.
*Stone cavity*.—Considered small in size, with flattened form and dimensions corresponding to the stone's dimensions.
*Stone surface*.—
*Surface texture*.—The pit is transversely furrowed on its entire surface. Furrows are deeper and more oblate on lateral sides.
*Ridges*.—The surface texture is generally characterized by more prominent ridges along the ventral edges and at the apical tip.
*Ventral edge*.—
*Width*.—Approximately 2.5 millimeters at mid-suture.
*Dorsal edge*.—
*Shape*.—Grooved.
*Stone color*.—The color of the dry stone is generally considered light orange brown (RHS Greyed Orange 165 B or RHS Greyed Orange 165 C).
*Tendency to split*.—Splitting is very low or absent, depending on climatic conditions between blooming period and stone hardening.
*Kernel*.—
*Size*.—The kernel is considered small.
*Length*.—Approximately 8.0 to 9.0 millimeters.
*Width*.—Approximately 9.0 to 10.0 millimeters.
*Thickness*.—Approximately 8.0 to 9.0 millimeters.
*Form*.—Considered flattened and elliptic. Sometimes double.
*Pellicle*.—The pellicle of the kernel has a short pubescence.
*Color*.—The kernel skin is orange-brown colored (RHS Greyed Orange N167 A). The almond, which is the seed of the kernel, is white (RHS White 155 B) and has a bitter tasting. The kernel and its embryo are mature at the time of fruit maturity.
*Use*.—The subject variety 'CAKERUMBA' is considered to be a white flat nectarine tree of the medium or late season of maturity, and which produces fruits that are considered very firm, attractively colored with a very luminous purple red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.
*Keeping quality*.—Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.
*Shipping quality*.—Considered very good. The fruit of the new white flat nectarine variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.
*Resistance to insects and disease*.—No particular susceptibilities were noted. The present variety is not very sensitive to *Monilia* or rot. The pistil cavity is completely closed, generally without any cork formation.

Although the new variety of white flat nectarine tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of white flat nectarine tree as illustrated and described, characterized by fruits with high eating quality and very long shelf life without alteration before and after harvesting, with a semi-sweet white flesh, with a slightly red pigmentation around the stone cavity, a completely closed pistil cavity and an attractive luminous skin with a high percentage of purple red blush on skin surface, on a red background.

* * * * *